(12) United States Patent
Romano et al.

(10) Patent No.: US 8,725,539 B2
(45) Date of Patent: May 13, 2014

(54) SYSTEMS AND METHODS FOR PROVIDING A CONTINUUM OF CARE

(75) Inventors: David C. Romano, Beavercreek, OH (US); Linda Dinkel, Hamilton, OH (US)

(73) Assignee: Premier Health Care Services Inc., Dayton, OH (US)

( * ) Notice: Subject to any disclaimer, the term of this patent is extended or adjusted under 35 U.S.C. 154(b) by 230 days.

(21) Appl. No.: 13/227,075

(22) Filed: Sep. 7, 2011

(65) Prior Publication Data

US 2012/0059672 A1  Mar. 8, 2012

Related U.S. Application Data

(60) Provisional application No. 61/380,660, filed on Sep. 7, 2010.

(51) Int. Cl.
| | |
|---|---|
| *G06Q 10/00* | (2012.01) |
| *G06Q 50/00* | (2012.01) |
| *G06Q 40/00* | (2012.01) |
| *G06F 19/00* | (2011.01) |
| *A61B 5/00* | (2006.01) |
| *A61N 1/00* | (2006.01) |

(52) U.S. Cl.
USPC ........................................ 705/3; 705/2; 705/4

(58) Field of Classification Search
USPC ............................................................ 705/3
See application file for complete search history.

(56) References Cited

U.S. PATENT DOCUMENTS

| | | |
|---|---|---|
| 6,347,329 B1 | 2/2002 | Evans |
| 6,915,265 B1 | 7/2005 | Johnson |
| 7,076,436 B1 | 7/2006 | Ross, Jr. et al. |
| 7,302,398 B2 | 11/2007 | Ban et al. |
| 7,647,320 B2 | 1/2010 | Mok et al. |
| 7,716,071 B2 | 5/2010 | Gold |
| 7,844,560 B2 | 11/2010 | Krishnan et al. |
| 2001/0012913 A1* | 8/2001 | Iliff ................................ 600/300 |
| 2002/0103675 A1 | 8/2002 | Vanelli |
| 2004/0111294 A1* | 6/2004 | McNally et al. ................... 705/2 |
| 2004/0193019 A1 | 9/2004 | Wei |
| 2005/0080462 A1* | 4/2005 | Jenkins et al. ................... 607/58 |
| 2005/0197862 A1 | 9/2005 | Paterson et al. |
| 2005/0209891 A1 | 9/2005 | Jacobus et al. |
| 2007/0143141 A1 | 6/2007 | Villasenor et al. |
| 2008/0109252 A1 | 5/2008 | LaFountain |
| 2008/0183069 A1 | 7/2008 | Fujimoto |
| 2009/0070199 A1 | 3/2009 | Zamani |
| 2009/0164474 A1 | 6/2009 | Noumeir |
| 2009/0234628 A1 | 9/2009 | Yu et al. |
| 2010/0138199 A1 | 6/2010 | Soto et al. |
| 2010/0205008 A1 | 8/2010 | Hua et al. |
| 2011/0142828 A1 | 6/2011 | Uhlen et al. |

\* cited by examiner

*Primary Examiner* — Hiep V Nguyen

(74) *Attorney, Agent, or Firm* — Dinsmore & Shohl, LLP

(57) ABSTRACT

Disclosed herein are embodiments for providing a continuum of care. At least one embodiment includes receiving patient information for a patient, the patient information including medical information of the patient suffering from a specific medical condition and determining whether the patient qualifies for the continuum of care. Similarly, some embodiments include, in response to determining that the patient qualifies for the continuum of care, facilitating a primary patient screening to determine whether the patient has a tangential medical condition. Still some embodiments include creating a continuum of care plan for the patient that utilizes the patient information and results of the primary screening to predict a future medical care need of the patient.

20 Claims, 13 Drawing Sheets

FILE  EDIT  FAVORITES  TOOLS  HELP
BACK  SEARCH ★FAVORITES
ADDRESS [                                                    ] →GO

NAME: [JANE DOE]
SSN: [        ] AGE: [    ]
ADDRESS: [        ]
CITY: [        ]
STATE: [    ]  ZIP: [        ]

972

RESULTS OF PRELIMINARY SCREENING     RESULTS OF SECONDARY SCREENING

VISION PROBLEMS: 8*  **PROMPTED SECONDARY      DISTANCE PROBLEMS: 1
SCREENING                                      NEAR OBJECT PROBLEMS: 9
FALL RISK: 2                                   GLAUCOMA: 4
DEPRESSION: 3                                  CATARACTS: 5
HEARING: 1

CURRENT PRESCRIPTIONS: MED1, MED2

CURRENT SYMPTOMS: CHEST PAIN, SHORTNESS OF BREADTH

CURRENT DIAGNOSIS: CHEST PAINS CAUSED BY MILD HEART ATTACK, WHICH RESULTED FROM NOT
TAKING MED1 AS DIRECTED.  SUSPECTED THAT VISION PROBLEMS CAUSED THIS.

SELECTED MANAGER: MITCH ( SEE CONTINUUM OF CARE PLAN )  ⟵ 974

DONE

NAME: JANE DOE
AGE: 83
MANAGER: MITCH

CONTINUUM OF CARE PLAN:

1. TAKE TWO DOSES OF PRESCRIBED MEDICATION ONCE A DAY.

2. RETURN TO GREEN ACRES ASSISTED LIVING FOR 12 MONTHS BEFORE REASSESSMENT.

3. RETURN TO DR. SMITH (CARDIOLOGIST) EVERY SIX MONTHS

4. RETURN TO DR. SPECS (OPHTHALMOLOGIST) EVERY SIX MONTHS.

[ACCEPT CONTINUUM OF CARE PLAN] — 1072

[EDIT CONTINUUM OF CARE PLAN] — 1074

[CANCEL CONTINUUM OF CARE PLAN] — 1076

FIG. 10

PATIENTS

JANE DOE AGE: 83 CURRENT MEDICATIONS: MED1, MED2, MED3

CURRENT APPOINTMENTS: DR. SMITH (CARDIO) ON 9.1.11, DR. SPECS (OPTHO) ON 9.15.11

CURRENT MEDICAL ISSUES: CHEST PAIN, SHORTNESS OF BREATH, VISION PROBLEMS

PREDICTED MEDICAL ISSUES: LIKELY CATARACTS, VISION DEGRADATION

TASKS: VISIT MRS. DOE ONCE A DAY TO ASSIST IN HER TAKING MEDICATIONS

JOHN MAGOO AGE: 97 CURRENT MEDICATIONS: MED1, MED2

CURRENT APPOINTMENTS: DR. JONES (GP) ON 9.3.11, DR. SPECS (OPTHO) ON 9.15.11, DR. DOWN (PSYCH) ON 9.22.11

CURRENT MEDICAL ISSUES: BLINDNESS, PAIN IN LEFT LEG, DEPRESSION

PREDICTED MEDICAL ISSUES: PAIN IN LEFT LEG LIKELY TO INCREASE, LIKELY WHEELCHAIR USER.

TASKS: CONTACT MR. MAGOO'S RELATIVES FOR DAILY MONITORING

FIG. 11

TODAY'S PATIENTS

JANE DOE
AGE: 83 CURRENT MEDICATIONS: MED1, MED2, MED3

CURRENT SYMPTOMS: MRS. DOE APPEARS TO HAVE VISION PROBLEMS FOR OBJECTS THAT ARE LESS THAN 6 FEET AWAY. MRS. DOE DOES NOT APPEAR TO HAVE GLAUCOMA PROBLEMS AND ONLY MODERATE CATARACTS.

[ SEE CONTINUUM OF CARE PLAN ] — 1272          1274 — [ ENTER DIAGNOSIS AND TREATMENT ]

JOHN MAGOO
AGE: 97 CURRENT MEDICATIONS: MED1, MED2

CURRENT SYMPTOMS: MR. MAGOO APPEARS TO HAVE BOTH NEAR RANGE AND DISTANCE VISIO ISSUES TO THE POINT OF BLINDNESS. GLAUCOMA AND CATARACTS BOTH APPEAR TO BE AN ISSUE AS WELL.

[ SEE CONTINUUM OF CARE PLAN ] — 1276          1278 — [ ENTER DIAGNOSIS AND TREATMENT ]

FIG. 12

SYSTEMS AND METHODS FOR PROVIDING A CONTINUUM OF CARE

CROSS REFERENCE

This application claims the benefit of U.S. Provisional Application No. 61/380,660, filed Sep. 7, 2010 which is incorporated by reference in its entirety.

BACKGROUND

1. Field

Embodiments provided herein generally relate to providing medical care for individuals, and particularly to facilitating communication among a plurality of medical care providers to more efficiently treat and predict patient care requirements.

2. Technical Background

Many people, including elderly people, have various medical needs that may be handled by one or more different medical service providers. Oftentimes these service providers have no infrastructure for communication of information regarding these patients. As such, a patient may develop a medical condition that could have been anticipated by one of the service providers, but is never communicated to any other medical provider. Due to the lack of communication among the service providers, the effectiveness in treating the medical condition may be reduced due to the delay. Additionally, oftentimes patients return to a physician or emergency department multiple times for the same medical condition because the actual cause of the medical condition is never communicated to the treating physician.

SUMMARY

Disclosed herein are embodiments for providing a continuum of care. At least one embodiment includes receiving patient information for a patient, the patient information including medical information of the patient suffering from a specific medical condition and determining whether the patient qualifies for the continuum of care. Similarly, some embodiments include, in response to determining that the patient qualifies for the continuum of care, facilitating a primary patient screening to determine whether the patient has a tangential medical condition. Still some embodiments include creating a continuum of care plan for the patient that utilizes the patient information and results of the primary screening to predict a future medical care need of the patient.

Additionally included are embodiments of a system for providing a continuum of care. Some embodiments of the system include a memory component that stores a program that, when executed by the system, causes the system to receive patient information for a patient, the patient information including medical information of the patient suffering from a specific medical condition and determine whether the patient qualifies for the continuum of care. In some embodiments, the program causes the system to, in response to determining that the patient qualifies for the continuum of care, receive data for a primary patient screening to determine whether the patient has a tangential medical condition and, in response to determining that the patient has the tangential medical condition, receive data for a secondary patient screening to determine an extent of the tangential medical condition. In still some embodiments, the program causes the system to create a continuum of care plan for the patient that utilizes the patient information and results of the primary screening to predict a future medical care need of the patient, where the continuum of care plan coordinates patient care with a plurality of different health care providers.

Similarly, embodiments of a non-transitory computer-readable medium may include logic that causes a computing device to receive patient information for a patient. The patient information may include medical information of the patient suffering from a specific medical condition and determine whether the patient qualifies for the continuum of care. In some embodiments, the logic causes the computing device to create a continuum of care plan for the patient that utilizes the patient information and results of the primary screening to predict a future medical care need of the patient, wherein the continuum of care plan coordinates patient care with a plurality of different health care providers and provide a user interface for accessing the continuum of care plan, where the user interface includes an option to edit the continuum of care plan.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 9 depicts a user interface for creating a continuum of care plan for a patient, according to embodiments shown and described herein;

FIG. 10 depicts a user interface of a continuum of care plan for a patient, according to embodiments shown and described herein;

FIG. 11 depicts a user interface for providing a patient manager with a plurality of patients with whom the patient manager works, according to embodiments shown and described herein;

FIG. 12 depicts a user interface for a medical professional to view the continuum of care plan for a patient, according to embodiments shown and disclosed herein.

DETAILED DESCRIPTION

Embodiments disclosed herein may include a patient care computing device that is coupled to one or more medical establishments. In some embodiments, the patient care computing device may be configured to provide a user interface (via local software and/or an internet site) for a technician to submit information regarding a patient. Additionally, the patient care computing device may be configured to communicate with the medical establishments to determine previous medical care provided to the patient. From this information, the patient care computing device may determine probable future needs for the patient, as well as the medical facilities that are best equipped to provide care for those needs. With this information, the patient care computing device can develop a continuum of care plan for the patient to address at least one current and future medical need of that patient.

Similarly, in some embodiments, the patient care computing device may be configured to determine availability at the medical facilities for accommodating the patient, as well as determine costs, insurance applicability, length of stay, and/or provide other services to provide the patient with information for making an appropriate decision regarding future care. Still some embodiments may be configured to interface with the determined medical facilities to make appointments for the patient to receive care at that medical facility. These and other embodiments are discussed in more detail, below.

Figure 1:
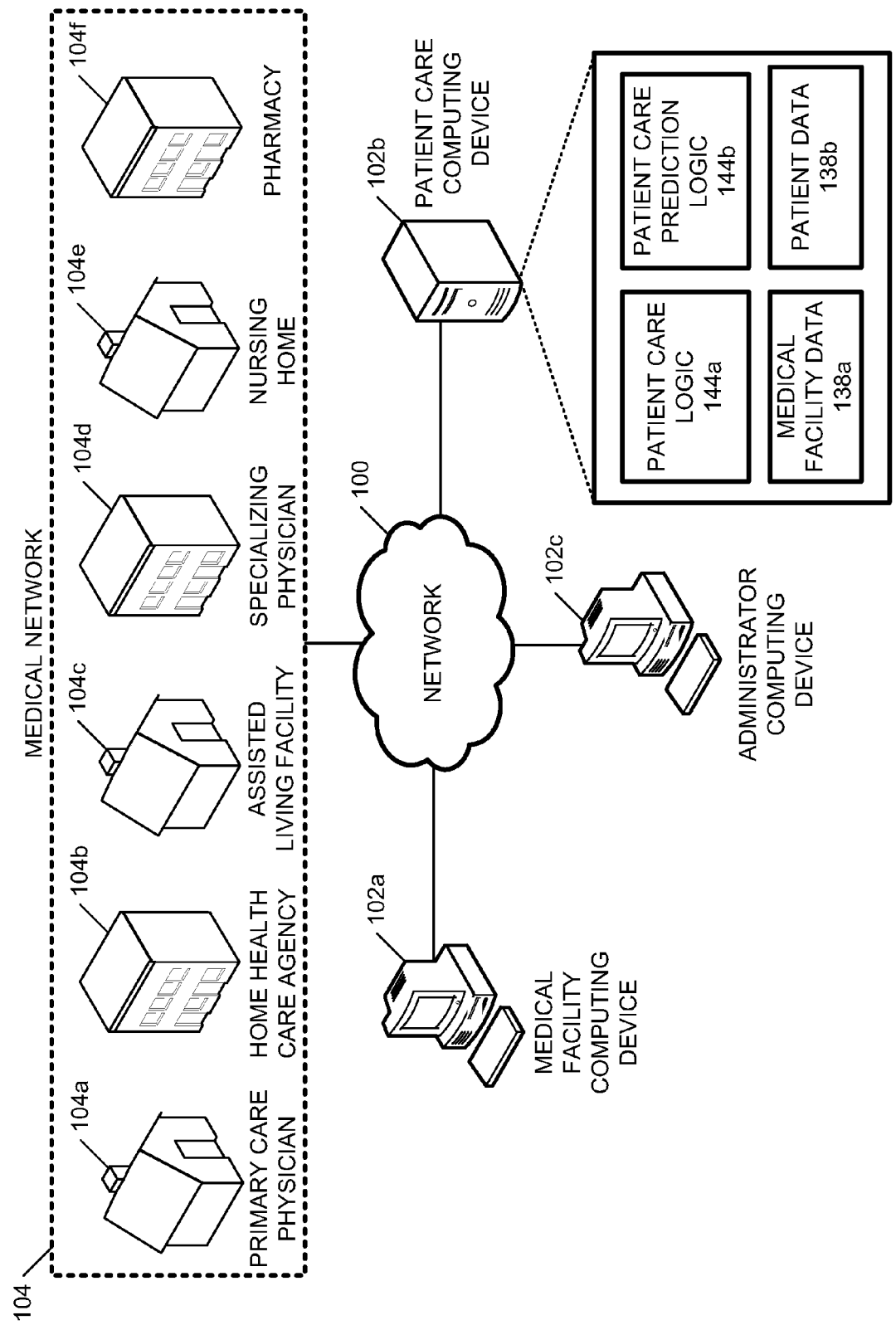
FIG. 1 depicts an exemplary computing environment, illustrating components for a system that provides a continuum of care, according to embodiments shown and described herein.

Referring now to the drawings, FIG. 1 depicts an exemplary computing environment, illustrating components for a system that provides a continuum of care, according to embodiments shown and described herein. As illustrated in FIG. 1, a network 100 may include a wide area network, such as the Internet, a local area network (LAN), a mobile communications network, a public service telephone network (PSTN) and/or other network and may be configured to electronically couple a medical facility computing device 102a, a patient care computing device 102b, and an administrator computing device 102c. Also coupled to the network 100 is a plurality of medical facilities. The plurality of medical facilities may or may not be unrelated but are tied together into a medical network 104 through use of the patient care computing device 102b and the continuum of care plan. The medical facilities may include a primary care physician 104a, a home health care agency 104b, an assisted living facility 104c, a specializing physician 104d, a nursing home 104e, and a pharmacy 104f. Other medical facilities, such as a social services department, may also be included in the medical network 104, but are excluded here for simplicity.

Similarly, the medical facility computing device 102a may be located at an emergency department, such as at a hospital, doctor's office, research center, community resource facility, and/or may be a user device, such as a personal computer, laptop computer, mobile telephone, tablet, etc. Additionally, the medical facility computing device 102a may be configured to receive, store, and/or send medical data regarding one or more patients. This medical data may include medical records, such as diagnoses, treatments, prescriptions, etc.

Similarly, the patient care computing device 102b may include patient care logic 144a, patient care prediction logic 144b, medical facility data 138a, and a registry of patient data 138b. As described in more detail below, the patient care logic 144a may be configured to cause the patient care computing device 102b to determine appropriate care for a patient, such as a continuum of care plan, which may include determining medical facilities, prescriptions, and/or other information. Similarly, the patient care prediction logic 144b may be further configured to predict future care for a patient, including determining medical facilities, prescriptions, and/or other information. In making these determinations, the patient care logic 144a and the patient care prediction logic 144b may access medical facility data 138a and the registry of patient data 138b, as described in more detail, below.

As an example, a patient may have a medical procedure performed at the county hospital. The patient care computing device 102b may receive this data and determine whether any additional medical care is likely. If so, the patient care computing device 102b can determine the additional medical care, as well as a facility that can provide that medical care. Similarly, in some embodiments, this data may be sent to the patient, a patient manager, and/or to a medical facility staff member. Some embodiments may be configured to automatically create an appointment for the patient at the determined facility.

Additionally included in FIG. 1 is the administrator computing device 102c. In the event that the patient care computing device 102b requires oversight, updating, or correction, the administrator computing device 102c may be configured to provide the desired oversight, updating, and/or correction.

It should be understood that while the medical facility computing device 102a, the patient care computing device 102b, and the administrator computing device 102c are depicted as personal computers and/or servers, these are merely examples. More specifically, in some embodiments any type of computing device (e.g. mobile computing device, personal computer, server, etc.) may be utilized for any of these components. Additionally, while each of these computing devices is illustrated in FIG. 1 as a single piece of hardware, this is also an example. More specifically, each of the computing devices 102a-102c may represent a plurality of computers, servers, databases, etc.

Figure 2:
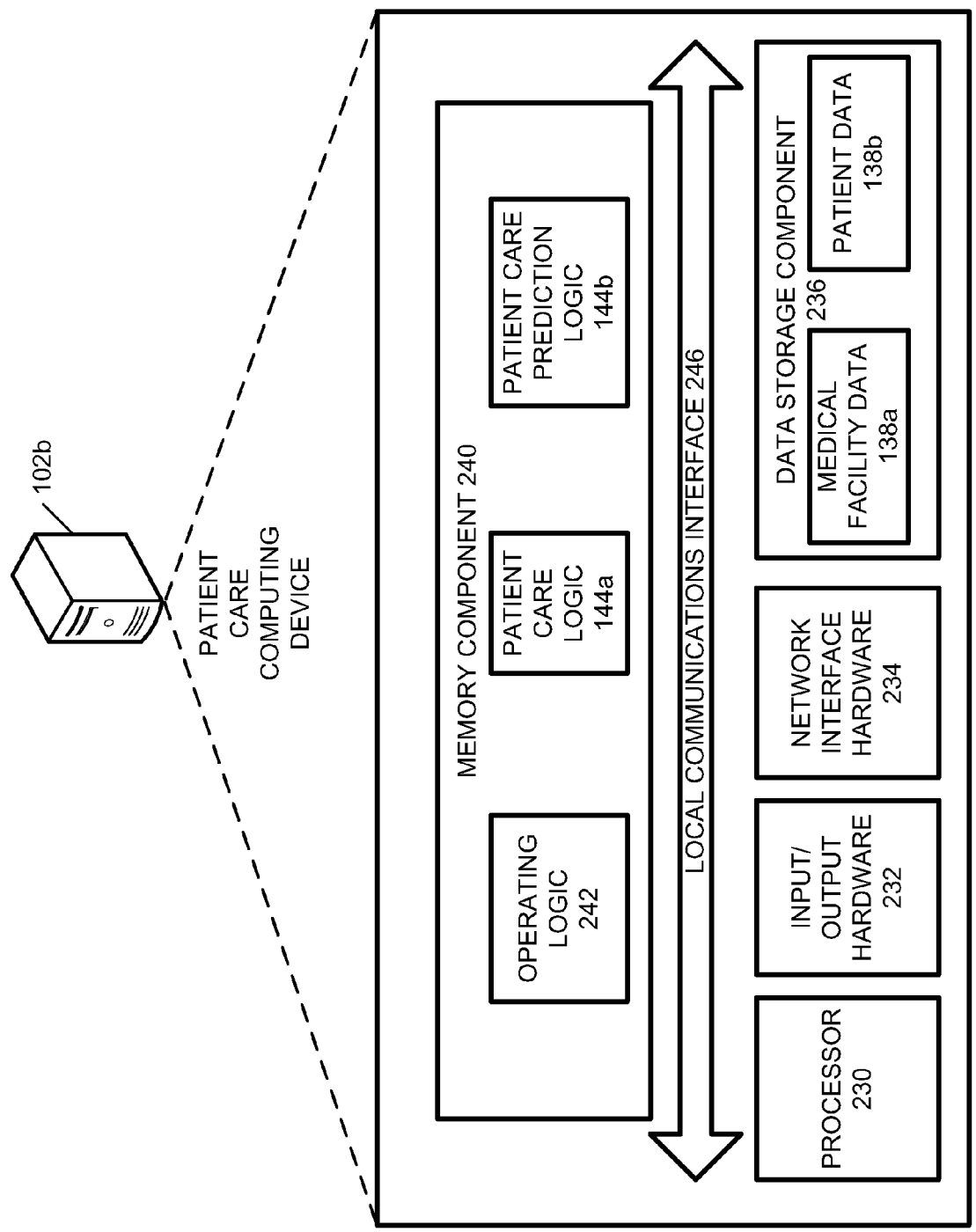
FIG. 2 depicts a patient care computing device that may be configured to provide parameters for patient care, according to embodiments disclosed herein.

FIG. 2 depicts a patient care computing device 102b that may be configured to provide parameters for patient care, according to embodiments disclosed herein. In the illustrated embodiment, the patient care computing device 102b includes a processor 230, input/output hardware 232, network interface hardware 234, a data storage component 236 (which stores the medical facility data 138a and the registry patient data 138b), and a memory component 240. The memory component 240 may be configured as volatile and/or nonvolatile memory and, as such, may include random access memory (including SRAM, DRAM, and/or other types of RAM), flash memory, registers, compact discs (CD), digital versatile discs (DVD), and/or other types of non-transitory computer-readable mediums. Depending on the particular embodiment, these non-transitory computer-readable mediums may reside within the patient care computing device 102b and/or external to the patient care computing device 102b.

Additionally, the memory component 240 may be configured to store operating logic 242, the patient care logic 144a and the patient care prediction logic 144b, each of which may be embodied as a computer program, firmware, and/or hardware, as an example. A local communications interface 246 is also included in FIG. 2 and may be implemented as a bus or other interface to facilitate communication among the components of the patient care computing device 102b.

The processor 230 may include any processing component operable to receive and execute instructions (such as from the data storage component 236 and/or memory component 240). The input/output hardware 232 may include and/or be configured to interface with a monitor, keyboard, mouse, printer, camera, microphone, speaker, and/or other device for receiving, sending, and/or presenting data. The network interface hardware 234 may include and/or be configured for communicating with any wired or wireless networking hardware, such as an antenna, a modem, LAN port, wireless fidelity (Wi-Fi) card, WiMax card, mobile communications hardware, and/or other hardware for communicating with other networks and/or devices. From this connection, communication may be facilitated between the patient care computing device 102b and other computing devices.

Similarly, it should be understood that the data storage component 236 may reside local to and/or remote from the patient care computing device 102b and may be configured to store one or more pieces of data for access by the patient care computing device 102b and/or other components.

Included in the memory component 240 are the operating logic 242, the patient care logic 144a, and the patient care prediction logic 144b. The operating logic 242 may include an operating system and/or other software for managing components of the patient care computing device 102b. Similarly, the patient care logic 144a may reside in the memory component 240 and may be configured to cause the processor 230 receive medical facility data, patient data, and/or other data. The patient care logic 144a may utilize this data to determine appropriate care for the patient. The care may include a determination of a medical facility for the next treatment, and/or other determinations. Additionally, the patient care prediction logic 144b may be configured to cause the processor 230 to receive similar data and predict future treatment for a patient to create a continuum of care plan, based on past treatments.

It should be understood that the components illustrated in FIG. 2 are merely exemplary and are not intended to limit the scope of this disclosure. While the components in FIG. 2 are illustrated as residing within the patient care computing device 102b, this is merely an example. In some embodiments, one or more of the components may reside external to the patient care computing device 102b. It should also be understood that, while the patient care computing device 102b in FIGS. 1 and 2 is illustrated as a single computing device, this is also merely an example. In some embodiments, the patient care functionality is implemented separately from the patient care prediction functionality, which may be implemented with separate hardware, software, and/or firmware.

It should also be understood that while the patient care computing device 102b is illustrated with both the patient care logic 144a and the patient care prediction logic 144b, this is also an example. In some embodiments, a single piece of logic may perform the functionality described for both the patient care logic 144a and the patient care prediction logic 144b. Similarly, in some embodiments, this functionality may be distributed to a plurality of different pieces of logic, which may reside in the patient care computing device 102b and/or elsewhere.

Figure 3:
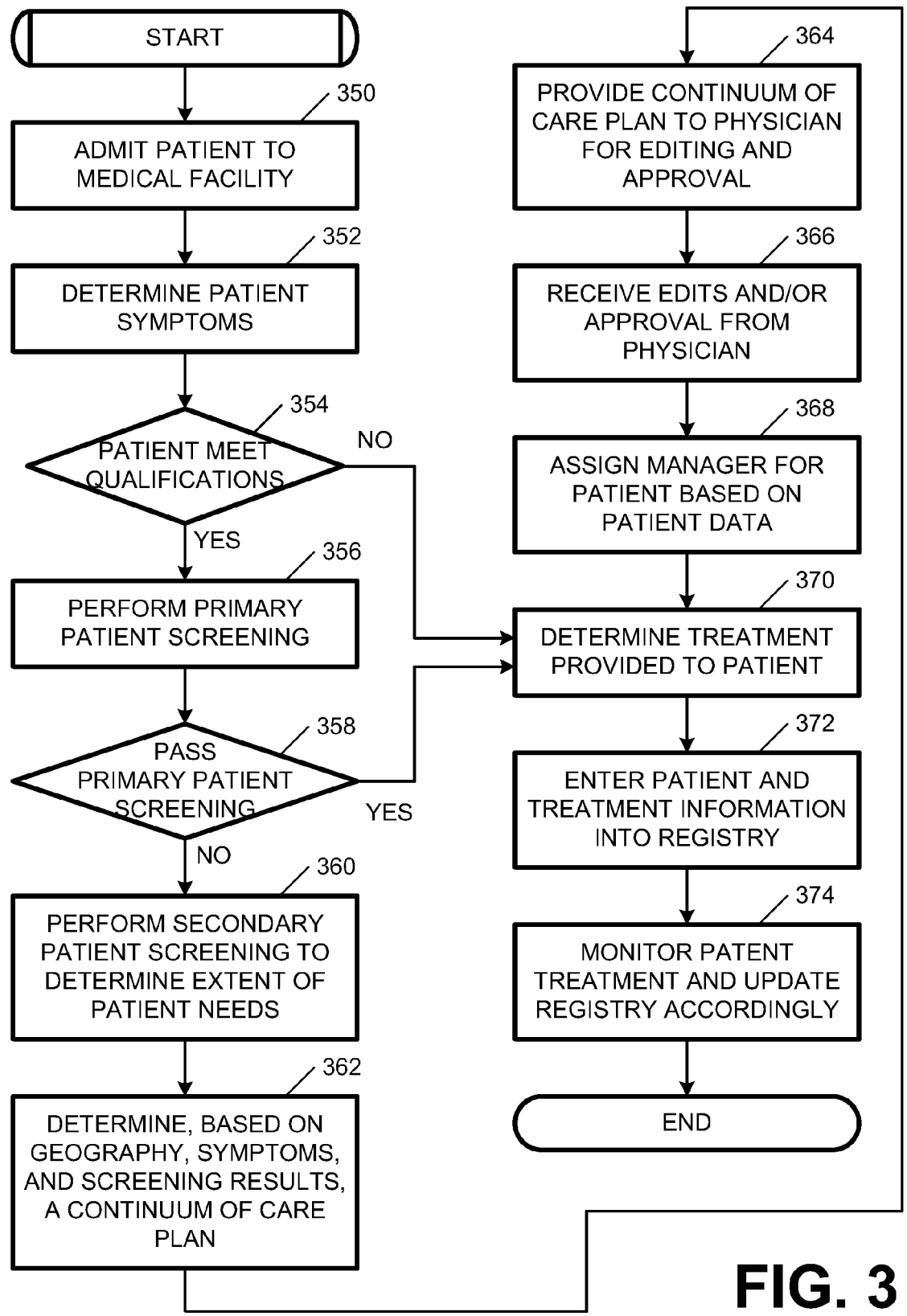
FIG. 3 depicts a flowchart for creating a patient registry and monitoring patient treatment, as described in the in the continuum of care plan, according to embodiments shown and disclosed herein.

FIG. 3 depicts a flowchart for creating a patient registry and monitoring patient treatment, as described in the in the continuum of care plan, according to embodiments shown and disclosed herein. As illustrated in block 350, a patient may be admitted into a medical facility. As discussed above, the medical network may include an emergency department, a general care physician office, a specializing physician office, and/or other medical facility that includes the medical facility computing device 102a. As such, in block 352, a determination of the patient symptoms may be made. In some embodiments, this determination may be made by the user filling out a form and a medical staff member entering the information into the medical facility computing device. In some embodiments however, the patient may enter this information directly into the system through a mobile device and/or other patient controlled computing device. In still some embodiments the physician may enter the information after performing a medical examination.

Regardless, in block 354, a determination may be made regarding whether the patient meets the requisite qualifications for creating a continuum of care plan. Depending on the particular embodiment, the continuum of care plan may be restricted to elderly patients and thus an age qualification may be implemented. If the patient does not meet the requisite qualifications, the process proceeds to block 370, described below.

If the patient does meet the requisite qualifications, then in block 356, a primary patient screening may be performed. The primary patient screening may include a vision test, hearing test, fall risk test, depression test, an abuse and neglect test, an altered mental status test, an abdominal pain test, a chest pain test, a lung disease test, a heart test, diabetes test, a Dyspnea test, a fever test, a pneumonia test, a stroke test, a mobility test, and/or other test to determine the patient's current ability to function. In block 358, a determination is made regarding whether the patient passed the primary patent screening. If so, the process may proceed to block 370. If the patient does not pass the primary patient screening, then in block 360, a secondary patient screening may be performed to determine the extent of the patient needs. In block 362 a continuum of care plan may be determined from the patient's geography, symptoms, and screening results. As discussed in more detail, below, the continuum of care plan may include current medical appointments and/or treatments, as well as a future plan for the patient. In block 364, the continuum of care plan may be provided to the physician for editing and/or approval. In block 366, edits and/or approval of the continuum of care plan may be received from a physician or other medical professional. In block 368, a patient manager may be assigned to the patient, according to the continuum of care plan. More specifically, if due to the patient's medical condition, the patient requires the patient manager to regularly visit the patient to ensure that the patient is taking the prescribed medications, the patient manager may be selected based on expertise in the area, as well as proximity to the patient's residence.

Additionally, in block 370, the treatment for the patient's current symptoms may be determined. More specifically, at this point, the physician or other medical professional may treat the patient according to the patient's symptoms, as well as from the determined continuum of care plan. In block 372, the patient and patient treatment information may be entered into a registry. In block 374, the patient treatment may be monitored and the registry may be updated accordingly.

In the embodiment described above, the medical facility, such as the emergency department, is the portal for admitting patients into the medical facility and for dismissing patients back to the community. As an example, if a patient is admitted into the emergency department for a health condition, the patient may be subject to one or more screenings and may be treated by one or more physicians in the medical network. As the physicians report treatments and other data back into the registry, the medical facility (in this case the emergency department) can access this information and determine whether the patient has been adequately treated before dismissing the patient. If the patient has not been adequately treated according to the continuum of care plan, the medical facility may commission additional treatments. However, if the patient has been adequately treated, the patient may be dismissed to a nursing home, assisted living facility, caregiver, etc. Once dismissed, the nursing home, assisted living facility, caregiver, etc. may be provided with access to the condition and/or medical requirements for the patient.

Figure 4:
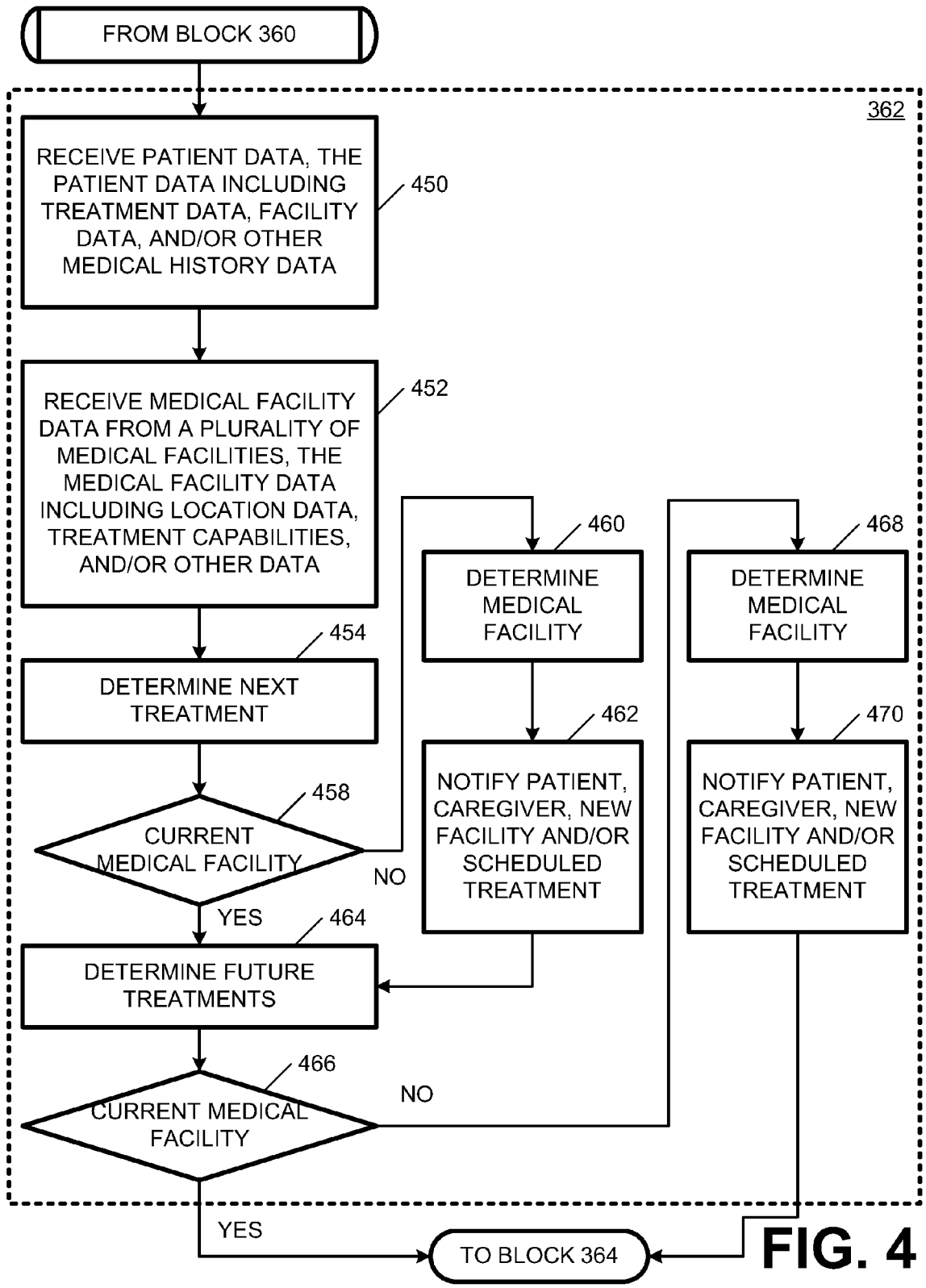
FIG. 4 depicts a flowchart for providing the continuum of care, according to embodiments shown and disclosed herein.

FIG. 4 depicts a flowchart for providing the continuum of care, according to embodiments shown and disclosed herein. More specifically, as illustrated in block 450, patient data including treatment data, data related to the facility that treated the patient, data regarding a location of the patient, data regarding allergies of the patient, and/or other data may be received. Similarly, in block 452, medical facility data may be received. The medical data facility may include location of a plurality of different medical facilities in the medical network, doctors at those medical facilities, medical equipment at the medical facilities, capabilities of the medical facilities, and/or other data related to the medical facilities. Similarly, in block 454, a next treatment (or plurality of treatments) in the continuum of care plan may be determined. The next treatment may include an appointment with a physician, a change in living condition (e.g., moving into a nursing home), and/or other action.

In block 458, a determination can be made regarding whether the medical facility that the patient is currently utilizing can provide the requisite treatment. If so, the process may proceed to block 464. If not, the process may proceed to block 460 to determine a medical facility that can provide the requisite treatment. At block 462, the patient, a caregiver, a patient manager, the current medical facility, the new medical facility, and/or other parties may be notified of the scheduled treatment. Additionally, in some embodiments, the treatment may be automatically scheduled by the patient care computing device for the patient in the new medical facility.

The process can then proceed to block 464 to predict future medical treatments. In block 466, a determination can be made regarding whether the current medical facility can provided the predicted services. If so, the process may end. If not, at block 468, a determination can be made regarding which medical facility can provide the predicted services. At block 470, the patient, a caregiver, the patient manager, the current medical facility, the new medical facility, and/or other parties may be notified of the scheduled treatments. Additionally, in some embodiments, a treatment may be automatically scheduled for the patient in the new medical facility.

As an example, if the current treatment for a patient is a hip replacement surgery, the patient care computing device 102b may be configured to access the medical facility data 138a (FIGS. 1, 2) to access data related to such a procedure. From this information, the patient care prediction logic 144b may utilize this information, along with the patient information to determine that the next likely medical treatment is six months of physical therapy. As the hospital that performed the surgery may not also provide physical therapy, a determination can be made regarding which medical facilities can provide physical therapy for hip replacement patients. Additionally, as the patient may also receive a prescription for pain medication, a determination regarding which pharmacies will likely be able to provide the prescription may also be determined.

Figure 5:
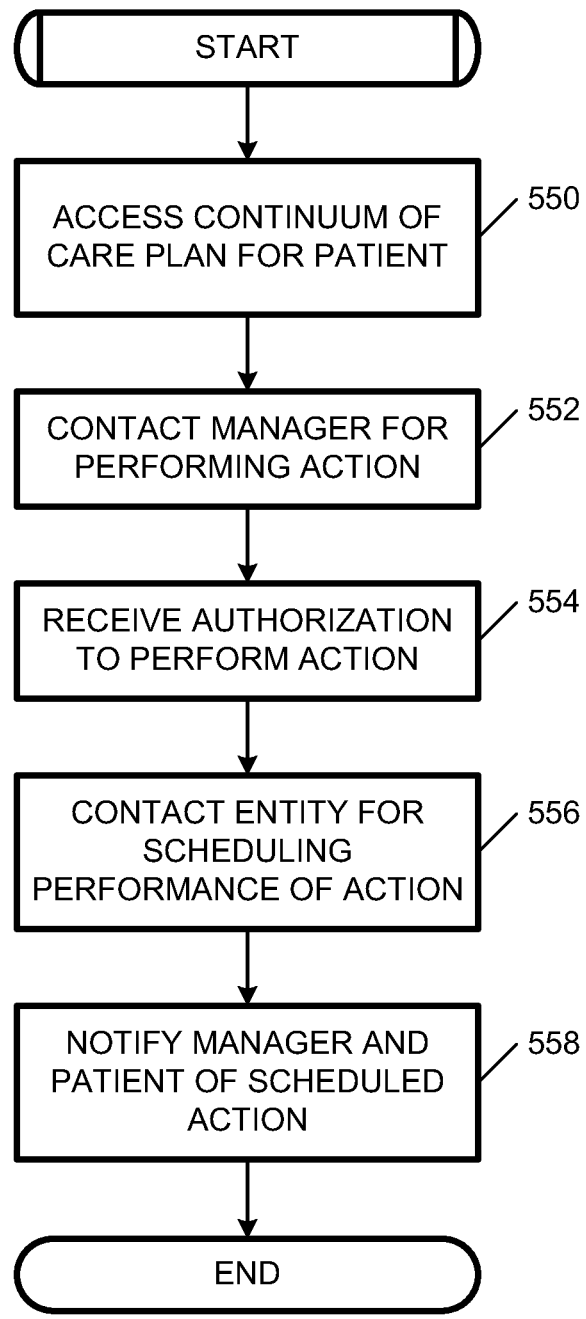
FIG. 5 depicts a flowchart for scheduling performance of an action, according to embodiments shown and described herein.

FIG. 5 depicts a flowchart for scheduling performance of an action, according to embodiments shown and described herein. As illustrated in block 550, a continuum of care plan for a patient may be accessed from a registry. In block 552, the patient manager of the patient may be contacted for performing the action. The action may include a medical appointment, a physical therapy appointment, etc. In block 554, if the patient manager approves the action as coinciding with the continuum of care plan, the patient manager authorization may be received. In block 556, an entity for scheduling the performance of the action may be contacted. More specifically, if the action is a medical appointment, the physician's office may be contacted to schedule the appointment. In block 558, the patient manager and patient may be notified of the scheduled action. At this point, the patient manager should be aware of the actions required to ensure that the patient is receiving the proper care according to the continuum of care plan.

Figure 6:
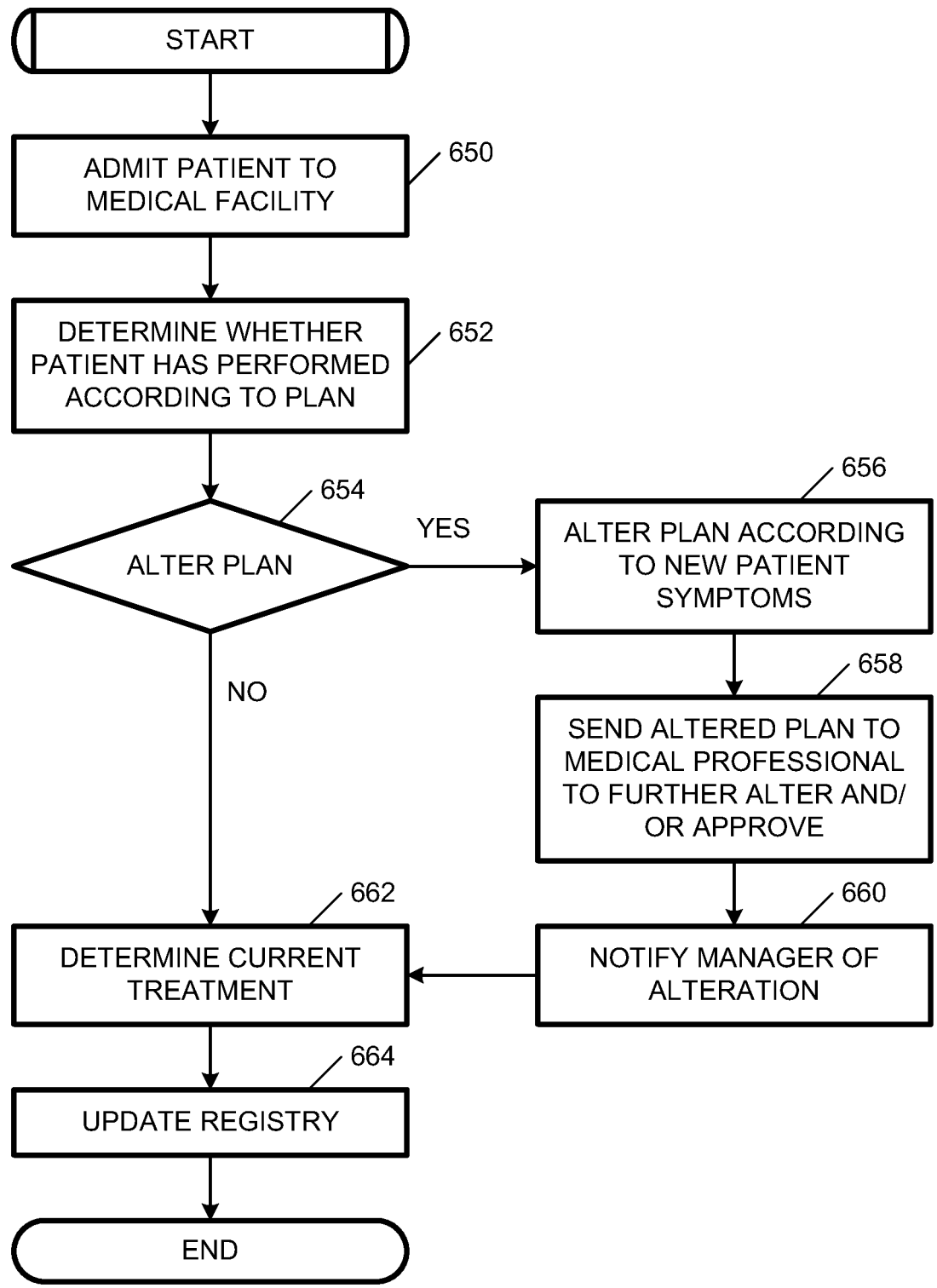
FIG. 6 depicts a flowchart for altering a continuum of care plan, according to embodiments shown and described herein.

FIG. 6 depicts a flowchart for altering a continuum of care plan, according to embodiments shown and described herein. As illustrated in block 650, the patient may be admitted into a medical facility. In block 652, a determination may be made regarding whether the patient has performed according to the continuum of care plan. More specifically, the patient manager may be contacted and/or other tests performed and compared with the continuum of care plan to determine whether the patient has been taking medications as prescribed and/or performing other suggested actions. In block 654, a determination may be made regarding whether to alter the continuum of care plan. Determining whether to alter the continuum of care plan may include determining whether the patient's medical condition has changed to require a change in the plan and/or determining whether the patient is willing and/or able to perform the suggested actions. If the continuum of care plan is not to be altered, the process may proceed to block 662. If the continuum of care plan is to be altered, in block 656, the continuum of care plan may be altered according to the patient's new symptoms (and/or other determinations). In block 658, the altered plan may be sent to the medical professional to further alter and/or approve the new plan. In block 660, the patient manager may be notified of the alteration. In block 662, a treatment for the patient's current symptoms may be determined and performed. In block 664, the registry may be updated.

Figure 7:
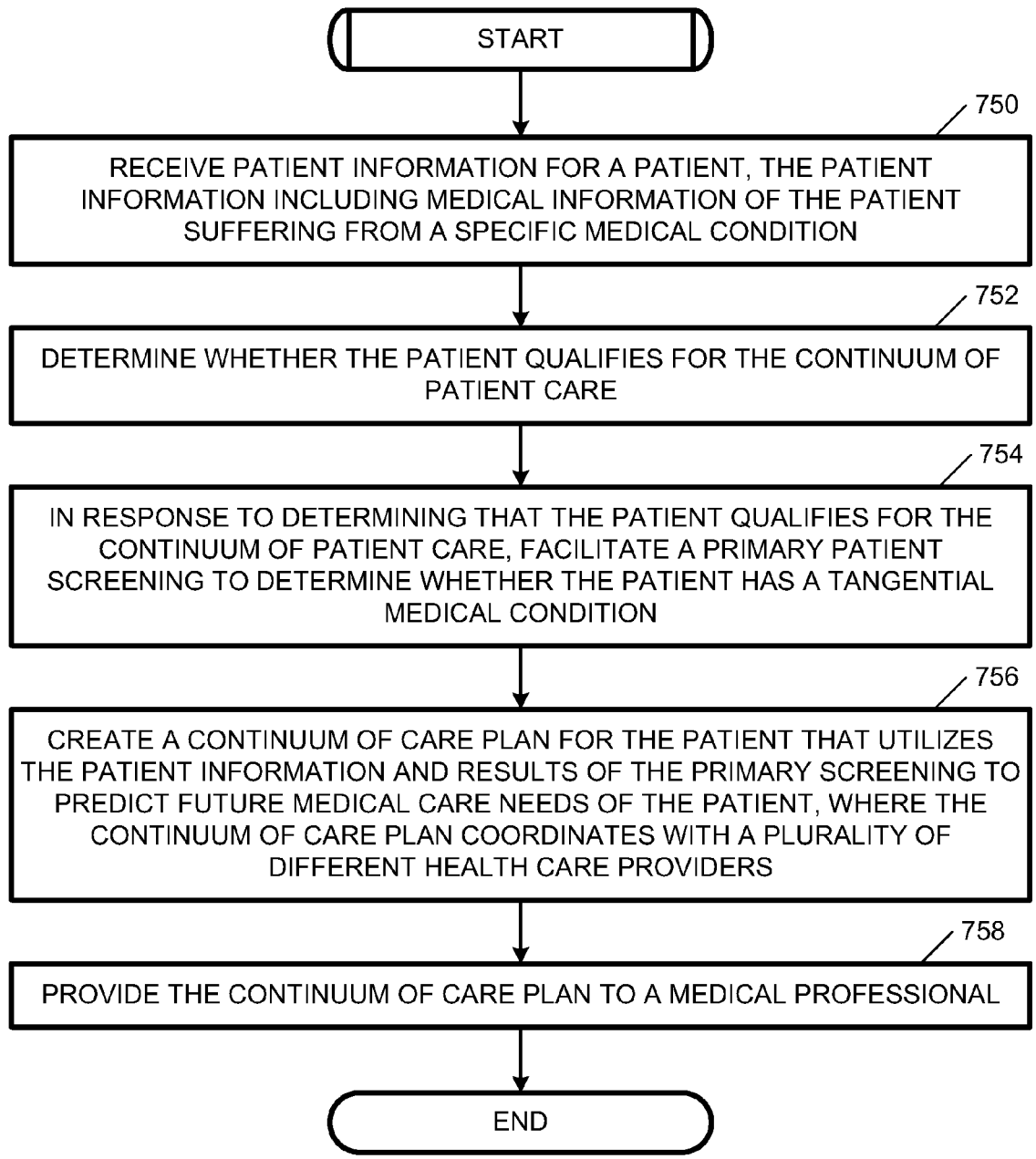
FIG. 7 depicts a flowchart for providing the continuum of care plan to a medical professional, according to embodiments shown and described here.

FIG. 7 depicts a flowchart for providing the continuum of care plan to a medical professional, according to embodiments shown and described here. As illustrated in block 750, patient information may be received from the patient. The patient information may include medical information of the patient suffering from a specific medical condition. More specifically, the patient may enter a medical facility with symptoms of a specific medical condition. This information, as well as medical history, allergies, residence, lifestyle habits, etc. may be received. In block 752, a determination may be made regarding whether the patient qualifies for the continuum of care. In some embodiments, the qualification may be related to age, while in some embodiments, the qualification may be related to other criteria, such as location, medical condition, etc.

Regardless, in block 754, in response to determining that the patient qualifies for the continuum of care, a primary patient screening may be performed and/or facilitated to determine whether the patient has a tangential medical condition. The tangential medical condition may include conditions related to vision, hearing, fall risk, depression, abuse and neglect, altered mental status, abdominal pain, chest pain, lung disease, heart problems, diabetes, Dyspnea, fever, pneumonia, stroke, mobility, etc., which could affect the patient's ability care for himself/herself in accordance with a physician's recommendations. Depending on the particular embodiment, the tangential medical condition may or may not be related to the specific medical condition. In block 756, a continuum of care plan may be created for the patient. The continuum of care plan may be created utilizing the patient information and results from the primary screening to predict future medical care needs of the patient. The continuum of care plan may be configured to coordinate with a plurality of different health care providers, such as those in the medical network 104 (FIG. 1). In block 758, the continuum of care plan may be provided to a medical professional for approval and/or editing. Additionally, the continuum of care plan may be provided to the patient, caregiver, manager, etc.

Figure 8:
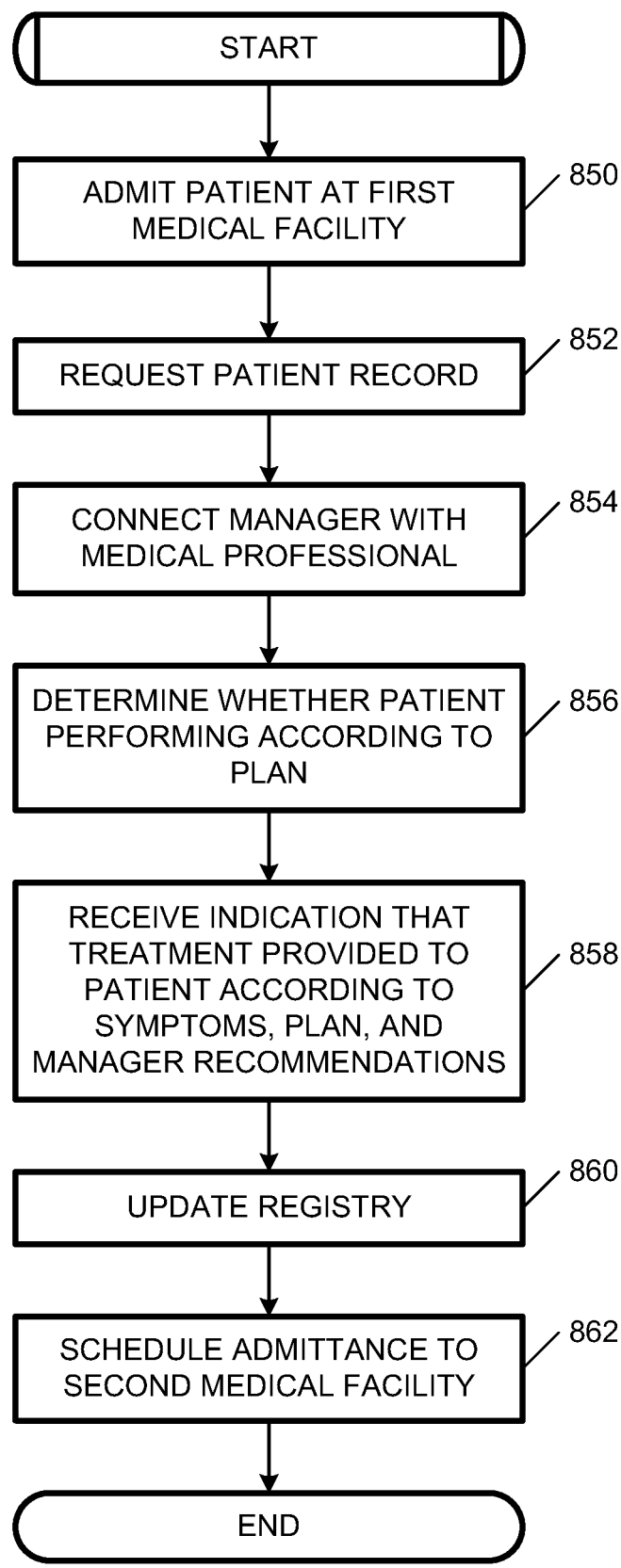
FIG. 8 depicts a flowchart for scheduling a patient into a plurality of medical network participants, according to embodiments shown and described herein.

FIG. 8 depicts a flowchart for scheduling a patient into a plurality of medical network participants, according to embodiments shown and described herein. As illustrated in block 850, a patent may be admitted at a first medical facility in the network participant. As discussed above, the medical network may include any of a plurality of different medical facilities. In block 852, a patient record may be requested. The patient record may be retrieved from the registry and may include the continuum of care and/or other information. In block 854, the patient manager of the patient may be connected with the treating medical professional to determine whether the patient is performing according to the continuum of care plan. In block 856, a determination is in fact made regarding whether the patient is performing according to the continuum of care plan. The physician may treat the patient and, in block 858, an indication that the patient has been treated according to the symptoms, the continuum of care plan, and the patient manager recommendations may be provided. In block 860, the registry may be updated with the new treatment data. In block 862, the patient may be scheduled for a medical appointment at a second medical facility in the medical network. More specifically, the patient care computing device 102b creates and coordinates the continuum of care plan among a plurality of different medical facilities. As such, the patient care computing device 102b may create the continuum of care plan, as well as schedule medical appointments among the entities in the medical network 104. Thus, after a first treatment is complete, a second treatment with a different medical facility may be scheduled in accordance with the continuum of care plan.

FIG. 9 depicts a user interface 970 for creating a continuum of care plan for a patient, according to embodiments shown and described herein. As illustrated, the user interface 970 may be configured for receiving patient information for creation of a continuum of care plan. More specifically, in area 972, the patient, a caregiver, medical personnel, and/or other entity may enter the patient information upon a patient being admitted to a medical facility, such as an emergency department. The patient may be admitted due to a specific medical condition (such as chest pain). If the patient meets the qualifications for creation of a continuum of care plan, the patient may be subject to a primary patient screening. As indicated above, the primary patient screening may determine whether the patient has any tangential medical issues. As such, the primary screening may include tests for vision, hearing, fall risk, depression, abuse and neglect, altered mental status, abdominal pain, chest pain, lung disease, heart, diabetes, Dyspnea, fever, pneumonia, stroke, mobility, and/or other tests. If the patient does not adequately complete one or more of the tests in the primary screening (in this case vision), a secondary screening may be prompted to further determine the nature and extent of the tangential medical issue. Other information may also be input into and provided within the user interface 970, such as current prescriptions, current symptoms, the physician's current diagnosis, and a selected patient manager.

More specifically, the physician at the medical facility may determine the other information and may provide a diagnosis and/or treatment for the patient. In the example depicted in FIG. 9, the physician determined that the chest pains were caused by a mild heart attack, which resulted from Mrs. Doe not taking Med1 as directed. However, due to the primary and secondary patient screenings, the physician determined that the likely cause of this issue was that Mrs. Doe cannot see the medication instructions and/or routinely locate the medications. As such, the patient care computing device 102b may determine a continuum of care plan, as well as select a patient manager for assisting in implementation of the continuum of care plan. An option 974 provided in the user interface 970 may direct the user of the user interface 970 to the continuum of care plan.

As an example, because the physician identified the cause of the chest pain as being related to Mrs. Doe's poor vision, this information may be utilized by the patient care computing device 102b (along with medical facility data 138a) to determine that patients of Mrs. Doe's age and with these symptoms will need an ophthalmologist appointment every 6 months. Accordingly, the continuum of care plan may include routine ophthalmologist appointments.

FIG. 10 depicts a user interface 1070 for providing a continuum of care plan for a patient, according to embodiments shown and described herein. As illustrated, the continuum of care plan may be provided and may include a plurality of actions for the patient to take. The actions may include appointments with physicians, reservations in nursing homes, and/or other actions, which may be facilitated and/or completed by the patient care computing device 102b. Also included in the user interface 1070 are an "accept continuum of care plan" option 1072, an "edit continuum of care plan" option 1074, and a "cancel continuum of care plan" option 1076. More specifically, the user interface 1070 may be provided to the physician and/or other medical personnel for accepting, editing, and/or cancelling the determined continuum of care plan. As an example, a physician may alter medications, treatments, facilities, managers, and/or other criteria to fully customize the continuum of care plan. Additionally, once the continuum of care plan is accepted, the patient care computing device 102b may automatically schedule the determined appointments, forward patient information to the appropriate medical facilities, and/or take other actions to implement the continuum of care plan.

FIG. 11 depicts a user interface 1170 for providing a patient manager with a plurality of patients with whom the patient manager works, according to embodiments shown and described herein. As illustrated, the patient manager may be provided with the user interface 1170, which includes patient information for each of those patients. In addition, the patient manager may be provided with reminders from the patient care computing device 102b, such that the patient manager never forgets tasks for any of the patients. Additionally, the patient manager may be informed of changes to any of the continuum of care plans. Other information and options may also be provided.

FIG. 12 depicts a user interface 1270 for a medical professional to view the continuum of care plan for a patient, according to embodiments shown and disclosed herein. As illustrated, the user interface 1270 may be forwarded to a medical professional, such as a physician prior to treating the patient. More specifically, the patient care computing device 102b may determine that the continuum of care plan for the patient includes an appointment with an ophthalmologist. The ophthalmologist may then receive the user interface 1270 to determine the information for treating the patient in accordance with the continuum of care plan. Additionally, options 1272, 1276 may be provided to the medical professional to view the continuum of care plan. Options 1274, 1278 may also be included for entering the medical professional's diagnosis and treatment. Once selected, this information may be sent to the patient care computing device 102b for updating the registry.

Figure 13:
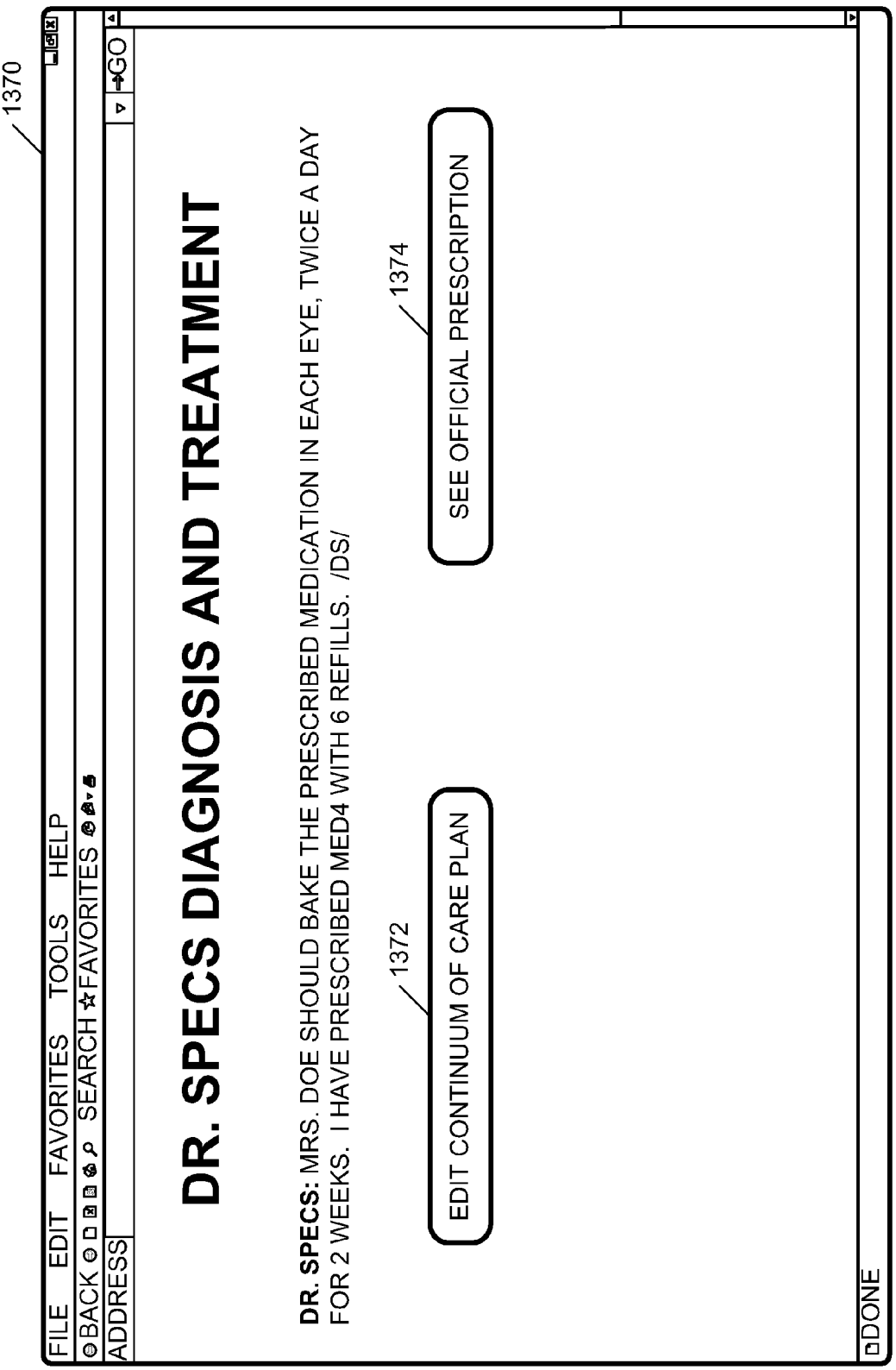
FIG. 13 depicts a user interface for a medical professional to input a new medical treatment and/or diagnosis, according to embodiments shown and disclosed herein.

FIG. 13 depicts a user interface 1370 for a medical professional to input a new medical treatment and/or diagnosis, according to embodiments shown and disclosed herein. In response to the physician or other medical professional entering the diagnosis and treatment from the user interface 1270 (FIG. 12), the medical professional may also prescribe one or more medications. As such, the prescriptions may also be uploaded to the patient care computing device 102b, which may then be viewed by other medical professionals that are treating the patient. Additionally, the prescription may also be sent to the patient's pharmacist, which can proceed with filing the prescription without the patient having to visit the pharmacy. Additionally, an option 1372 to edit the continuous plan and an option 1374 to see the official prescription may also be provided in the user interface 1370.

According to embodiments described herein, systems and methods for providing a continuum of care may provide a patient with a continuum of care plan that includes a plurality of different medical providers. By so doing, when a patient enters a medical facility, such as an emergency department, the treating physician will have information from each of the patient's other physicians, as well as the continuum of care plan so that the treating physician will be able to treat the patient without conflicting with another part of the continuum of care plan. This will provide the patient with a seamless experience among the various medical facilities, as well as allow the physicians, home health care agencies, assisted living facilities, nursing homes, pharmacies, etc. with the ability to know the patient's needs in advance and schedule accordingly.

While particular embodiments have been illustrated and described herein, it should be understood that various other changes and modifications may be made without departing from the spirit and scope of the claimed subject matter. Additionally, some embodiments are further disclosed in the Attachment. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method for providing a continuum of care comprising:
   receiving, by a computing device, patient information for a patient, the patient information comprising medical information of the patient suffering from a specific medical condition;
   determining, by the computing device, whether the patient qualifies for the continuum of care;
   in response to determining that the patient qualifies for the continuum of care, facilitating, by the computing device, a primary patient screening to determine whether the patient has a tangential medical condition that would require a different medical professional in a different medical field than the medical field of a current medical provider that is currently treating the patient;
   creating, by the computing device, a continuum of care plan for the patient that utilizes the patient information and results of the primary screening to predict a future medical care need of the patient, wherein the continuum of care plan provides a central oversight of the patient to coordinate patient care with a plurality of different health care providers; and
   providing, by the computing device, the continuum of care plan to the current medical professional.

2. The method of claim 1, further comprising, in response to determining that the patient has the tangential medical condition, performing a secondary screening to determine an extent of the tangential medical condition.

3. The method of claim 1, wherein creating the continuum of care plan comprises scheduling an appointment with at least one specializing physician to diagnose at least one of the following: the specific medical condition and the tangential medical condition.

4. The method of claim 1, wherein the plurality of different health care providers comprises at least two of the following: an emergency department, a primary care physician, a specializing physician, a home health care agency, an assisted living facility, a nursing home, a social services department, and a pharmacist.

5. The method of claim 1, further comprising assigning a patient manager for the patient, the patient manager being utilized to determine whether the continuum of care plan is properly implemented and that the patient is following the continuum of care plan, as instructed.

6. The method of claim 1, wherein the primary screening comprises a test for at least one of the following: vision, hearing, fall risk, depression, abuse and neglect, altered mental status, abdominal pain, chest pain, lung disease, heart problems, diabetes, Dyspnea, fever, pneumonia, stroke, and mobility.

7. The method of claim 1, further comprising providing a user interface for accessing the continuum of care plan, the user interface being provided to at least one of the following: an emergency department, a primary care physician, a specializing physician, a home health care agency, an assisted living facility, a nursing home, a social services department, and a pharmacist.

8. A system for providing a continuum of care comprising:
   a memory component that stores a program that, when executed by the system, causes the system to perform at least the following:
      receive patient information for a patient, the patient information comprising medical information of the patient suffering from a specific medical condition;
      determine whether the patient qualifies for the continuum of care;
      in response to determining that the patient qualifies for the continuum of care, receive data for a primary patient screening to determine whether the patient has a tangential medical condition that would require a different medical professional in a different medical field than the medical field of a current medical provider that is currently treating the patient;
      in response to determining that the patient has the tangential medical condition, receive data for a secondary patient screening to determine an extent of the tangential medical condition;
      create a continuum of care plan for the patient that utilizes the patient information and results of the primary screening to predict a future medical care need of the patient, wherein the continuum of care plan provides a central oversight of the patient to coordinate patient care with a plurality of different health care providers; and
      provide the continuum of care plan to the current medical professional.

9. The system of claim 8, wherein the program further causes the system to provide the continuum of care plan to a physician for editing and approval.

10. The system of claim 8, wherein creating the continuum of care plan comprises scheduling an appointment with at least one specializing physician to diagnose at least one of the following: the specific medical condition and the tangential medical condition.

11. The system of claim 8, wherein the plurality of different health care providers comprises at least two of the following: an emergency department, a primary care physician, a specializing physician, a home health care agency, an assisted living facility, a nursing home, a social services department, and a pharmacist.

12. The system of claim 8, wherein the program further causes the system to assign a patient manager for the patient, the patient manager being utilized to determine whether the continuum of care plan is properly implemented and that the patient is following the continuum of care plan, as instructed.

13. The system of claim 8, wherein the primary screening comprises a test for at least one of the following: vision, hearing, fall risk, depression, abuse and neglect, altered mental status, abdominal pain, chest pain, lung disease, heart problems, diabetes, Dyspnea, fever, pneumonia, stroke, and mobility.

14. The system of claim 8, wherein the program further causes the system to provide a user interface for accessing the continuum of care plan, the user interface being provided to at least one of the following: an emergency department, a primary care physician, a specializing physician, a home health care agency, an assisted living facility, a nursing home, a social services department, and a pharmacist.

15. A non-transitory computer-readable medium for providing a continuum of care that includes logic that, when executed by a computing device, causes the computing device to perform at least the following:
receive patient information for a patient, the patient information comprising medical information of the patient suffering from a specific medical condition that would require a different medical professional in a different medical field than the medical field of a current medical provider that is currently treating the patient;
determine whether the patient qualifies for the continuum of care;
create a continuum of care plan for the patient that utilizes the patient information and results of the primary screening to predict a future medical care need of the patient, wherein the continuum of care plan provides a central oversight of the patient to coordinate patient care with a plurality of different health care providers;
provide a user interface for accessing the continuum of care plan, wherein the user interface comprises an option to edit the continuum of care plan.

16. The non-transitory computer-readable medium of claim 15, wherein the logic further causes the computing device to, in response to determining that the patient qualifies for the continuum of care, facilitate a primary patient screening to determine whether the patient has a tangential medical condition, at least a portion of the primary patient screening being unrelated to the specific medical condition.

17. The non-transitory computer-readable medium of claim 16, wherein the logic further causes the computing device to perform a secondary screening to determine an extent of the tangential medical condition, in response to determining that the patient has the tangential medical condition.

18. The non-transitory computer-readable medium of claim 16, wherein the primary screening comprises a test for at least one of the following: vision, hearing, fall risk, depression, abuse and neglect, altered mental status, abdominal pain, chest pain, lung disease, heart problems, diabetes, Dyspnea, fever, pneumonia, stroke, and mobility.

19. The non-transitory computer-readable medium of claim 15, wherein the plurality of different health care providers comprises at least two of the following: an emergency department, a primary care physician, a specializing physician, a home health care agency, an assisted living facility, a nursing home, a social services department, and a pharmacist.

20. The non-transitory computer-readable medium of claim 15, wherein the logic further causes the computing device to assign a patient manager for the patient, the patient manager being utilized to determine whether the continuum of care plan is properly implemented and that the patient is following the continuum of care plan, as instructed.

* * * * *